United States Patent [19]

Matsutani et al.

[11] Patent Number: 5,012,066
[45] Date of Patent: Apr. 30, 1991

[54] METHOD OF AND APPARATUS FOR MANUFACTURING EYELESS SUTURE NEEDLE

[75] Inventors: Kanji Matsutani; Tadashi Otsuka, both of Takanezawa, Japan

[73] Assignee: Matsutani Seisakusho Co., Ltd., Takanezawa, Japan

[21] Appl. No.: 567,763

[22] Filed: Aug. 15, 1990

[30] Foreign Application Priority Data

Aug. 31, 1989 [JP] Japan .................................. 1-223123

[51] Int. Cl.$^5$ ............................................. B23K 26/00
[52] U.S. Cl. ............................ 219/121.68; 219/121.69
[58] Field of Search .................... 219/121.68, 121.69, 219/121.6, 121.85, 121.77

[56] References Cited

U.S. PATENT DOCUMENTS

| | | | |
|---|---|---|---|
| 4,700,043 | 10/1987 | Matsutani | 219/121.69 |
| 4,910,377 | 3/1990 | Matsutani et al. | 219/121.19 |
| 4,935,029 | 6/1990 | Matsutani et al. | 606/223 |

FOREIGN PATENT DOCUMENTS

| | | |
|---|---|---|
| 55-43691 | 3/1980 | Japan . |
| 59-110532 | 6/1984 | Japan . |
| 60-184485 | 9/1985 | Japan . |
| 63-55410 | 11/1988 | Japan . |

*Primary Examiner*—C. L. Albritton
*Attorney, Agent, or Firm*—Fish & Richardson

[57] ABSTRACT

For annealing a proximal end portion of a needle material for a suture needle, an energy beam is applied to a proximal end face of the needle material. There can be used a common oscillator which emits a laser beam for forming a gut-mounting hole in the proximal end portion of the needle material, and also emits a laser beam for effecting the above annealing. In this case, a converter is used for changing a path of travel of the laser beam. Namely, for forming the mounting hole, the laser beam from the oscillator is supplied to the proximal end face of the needle material through a condenser lens. For effecting the annealing, the laser beam is smoothed by a smoothing member, and is applied to the proximal end face of the needle material. In the case where the common oscillator is used, the needle material may be moved along the axis of the needle material.

13 Claims, 6 Drawing Sheets

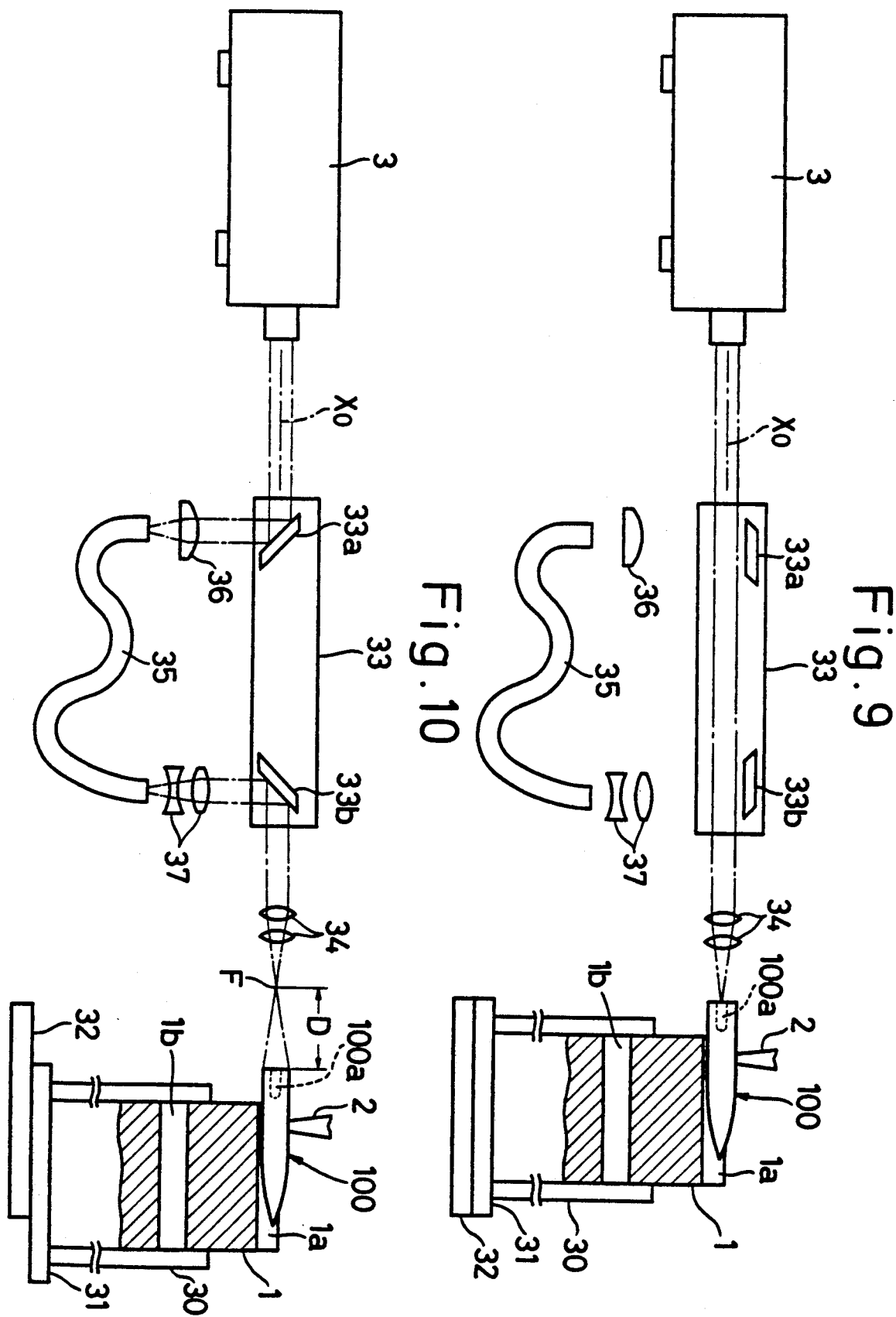

METHOD OF AND APPARATUS FOR MANUFACTURING EYELESS SUTURE NEEDLE

BACKGROUND OF THE INVENTION

This invention relates to a method of and apparatus for manufacturing an eyeless suture needle.

Instead of martensite-type stainless steel, austenite-type stainless steel has increasingly been used as a needle material for eyeless suture needles. Examples of such austenite-type stainless steel includes SUS304, SUS302 and SUS63151. Unlike martensite-type stainless steel, austenite-type stainless steel can not be hardened by quench hardening, and is usually hardened by work-hardening. Therefore, a wire material is cold-drawn and is hardened, and then is cut to produce needle materials. Subsequent steps are to point a distal end of the needle material, to form a mounting hole in a proximal end portion of the needle material, to insert a gut into the mounting hole and then to deform the proximal end portion of the needle material under pressure to fixedly secure the gut to the needle material, and to bend the needle material.

In order to deform the proximal end portion of the needle material to secure the gut to the needle material, the proximal end portion of the needle material is required to have a low hardness. If the hardness of the proximal end portion is high, the deformation of the proximal end portion can not be carried out satisfactorily. This may result in an unsatisfactory fixing of the gut to the needle material, and also may result in a situation in which part of the deformed proximal end portion is projected outwardly of the outer peripheral surface of the remainder, thereby adversely affecting the ability of the resultant suture needle to penetrate.

The needle material made of the austenite-type stainless steel is obliged to have a high hardness at the first stage as described above, and therefore it is necessary to sufficiently lower the hardness of the proximal end portion of the needle material by changing the crystals of the proximal end portion from a fiber-like elongated shape into a grain (particle)-like shape by means of annealing of the proximal end portion.

Japanese Utility Model Publication No. 25219/85 discloses a method in which an energy beam is applied to a needle material with its optical axis aligned with the axis of the needle material, thereby forming a mounting hole in the needle material, and thereafter a proximal end portion of the needle material is annealed using a burner. More specifically, a flame of the burner is applied to the outer peripheral surface of the proximal end portion of the needle material in a direction perpendicular or oblique to the axis of the needle material.

With this conventional method, however, the flame of the burner is unstable, and therefore there is a possibility that a very hard portion may remain at the proximal end portion of the needle material, in which case the proximal end portion can not be satisfactorily deformed under pressure. In order to avoid such disadvantage to sufficiently lower the hardness of the proximal end portion of the need material, the flame must be excessively applied to the outer peripheral surface of the proximal end portion of the needle material. As a result, the outer peripheral surface of the proximal end portion is roughened because of a local fusion thereof, and an oxide film is formed on this outer peripheral surface. Therefore, the needle material must be subjected to electropolishing for a long time, which results in a problem that the pointed distal end becomes dull, thus adversely affecting the penetrating ability of the needle.

Another problem of this conventional method is that the hardness of the needle material may be lowered over a region or length generally equal to or greater than the depth of the mounting hole. In other words, the portion of low hardness becomes excessively longer. This results in decrease of the strength of the proximal end portion of the needle material.

Japanese Patent Publication No. 55410/88 also discloses a method in which a flame of a burner is applied to a proximal end portion of a needle material in a direction perpendicular to the axis of the needle material, thereby annealing this proximal end portion.

U.S. Pat. No. 4,910,377 discloses a technique in which a mounting hole is formed in a proximal end portion of a needle material by an energy beam such as a laser beam and an electron beam.

Japanese Laid-Open (Kokai) Utility Model Application No. 43691/80 and Japanese Laid-Open Patent Application No. 184485/85 disclose a technique in which when forming a mounting hole in a proximal end portion of a needle material, the focus of a condenser lens is spaced or displaced from the proximal end portion of the needle material.

Japanese Laid-Open Patent Application No. 110532/84 discloses a device for supporting needle materials. This device comprises a rotary disk having V-shaped grooves, and a holder member.

U.S. Pat. No. 4,935,029 discloses a technique in which a needle material and a pipe material are welded together by an energy beam, and subsequently the welded portion, as well as the pipe material if necessary, is annealed by an energy beam. In this annealing method, however, the energy beam is applied in a direction perpendicular to the axis of the needle material, and the needle material is not only moved in its axial direction but also is rotated. In this method, the time required for the annealing is very long.

SUMMARY OF THE INVENTION

It is an object of this invention to provide a method of manufacturing a suture needle in which an ideal hardness distribution of a proximal end portion of a needle material can be achieved in a relatively short time by annealing, and the outer peripheral surface of the proximal end portion of the needle material is not unduly roughened.

Another object of the invention is to provide apparatus for performing such method.

According to one aspect of the present invention, there is provided a method of manufacturing an eyeless suture needle, comprising the steps of:

(a) forming a mounting hole in a proximal end face of a needle material in such a manner that the mounting hole extends along an axis of the needle material, a gut being adapted to be inserted into and fixed to the mounting hole; and (b) applying an energy beam to the proximal end face of the needle material to anneal a proximal end portion of the needle material.

According to another aspect of the invention, there is provided apparatus for manufacturing an eyeless suture needle comprising:

(a) emitting means for emitting a pulsed laser beam of parallel rays;

(b) support means for supporting a needle material in such a manner that the axis of the needle material is in alignment with the optical axis of the laser beam;

(c) condenser means for condensing the laser beam, the condenser means being disposed in the vicinity of a proximal end face of the needle material, supported by the support means, in such a manner that an axis of the condenser means is in alignment with the optical axis of the laser beam;

(d) smoothing means for smoothing the pulsed laser beam, the smoothing means being spaced from the optical axis of the laser beam;

(e) switching means disposed between the emitting means and the condenser means so as to switch a path of travel of the laser beam between a first light path and a second light path, the switching means first selecting the first light path and then selecting the second light path; when the laser beam from the emitting means travels along the first light path, the laser beam passing past the switching means to reach the condenser means, so that the laser beam condensed by the condenser means is applied to the center of the proximal end face of the needle material to thereby form a mounting hole in the proximal end face, a gut being adapted to be inserted into and fixed to the mounting hole; and when the laser beam from the emitting means travels along the second light path, the laser beam passing through the smoothing means to be smoothed and further passing through the condenser means to be applied to the proximal end face of the needle material to thereby anneal the needle material.

According to a further aspect of the invention, there is provided apparatus for manufacturing an eyeless suture needle comprising:

(a) emitting means for emitting a pulsed laser beam of parallel rays;

(b) support means for supporting a needle material in such a manner that the axis of the needle material is in alignment with the optical axis of the laser beam;

(c) condenser means for condensing the laser beam, the condenser means being disposed in the vicinity of a proximal end face of the needle material, supported by the support means, in such a manner that an axis of the condenser means is in alignment with the optical axis of the laser beam; and (d) moving means for moving the support means along the axis of the needle material between a first position and a second position, the support means being first disposed in the first position, and then being disposed in the second position; in the first position, the laser beam from the emitting means being condensed by the condenser means to be applied to the center of the proximal end face of the needle material to thereby form a mounting hole in the proximal end face, a gut being adapted to be inserted into and fixed to the mounting hole, and the proximal end face of the needle material being remoter from the focus of the condenser means in the second position than in the first position, so that the laser beams from the condenser means is spreaded over the proximal end face of the needle material to thereby anneal a proximal end portion of the needle material.

BRIEF DESCRIPTION OF THE DRAWINGS

FIG. 9 is a schematic view of a further modified apparatus shown in its mounting hole-forming mode; and FIG. 10 is a view similar to FIG. 9, but showing an annealing mode.

DESCRIPTION OF THE PREFERRED EMBODIMENTS OF THE INVENTION

A preferred embodiment of the invention will now be described with reference to the drawings. Reference is first made to a needle material 100 for an eyeless suture needle, used in this embodiment. A wire of austenite-type stainless steel is cold-drawn to bring its crystals into a fiber-like shape, thereby hardening the wire. Then, the drawn wire is cut into a predetermined length to provide the needle material 100 of an original shape having a circular cross-section. Then, one end of this needle material 100 is pointed.

Then, a mounting hole 100a is formed in the other or proximal end portion of the needle material 100, and extends along the axis of the needle material 100. More specifically, one pulse (whose pulse duration is, for example, 1 msec.) of a laser beam composed of parallel rays is outputted from a laser beam oscillator (not shown), and is condensed by a condenser lens, and is supplied to the center of the proximal end face of the needle material 100. The above pulse of the laser beam has a very high instantaneous peak value, and is concentrated on the center of the proximal end face of the needle material 100, and therefore that portion of the needle material 100 to which the laser beam is applied is sublimed, thereby creating the mounting hole 100a. The optical axis of the laser beam is in alignment with the axis of the needle material 100. The focus of the laser beam either coincides with the proximal end face of the needle material 100 or is slightly spaced from this proximal end face. The amount of this spacing is about 0.5 mm at the maximum in the case where the depth of the mounting hole 100a is 1.25 mm.

Figure 1:
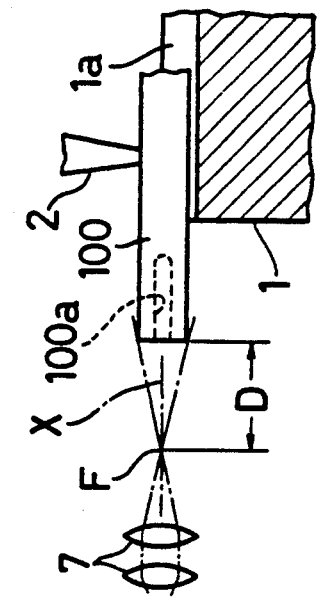
FIG. 1 is a schematic view of a needle manufacturing apparatus according to the present invention.
Figure 1:
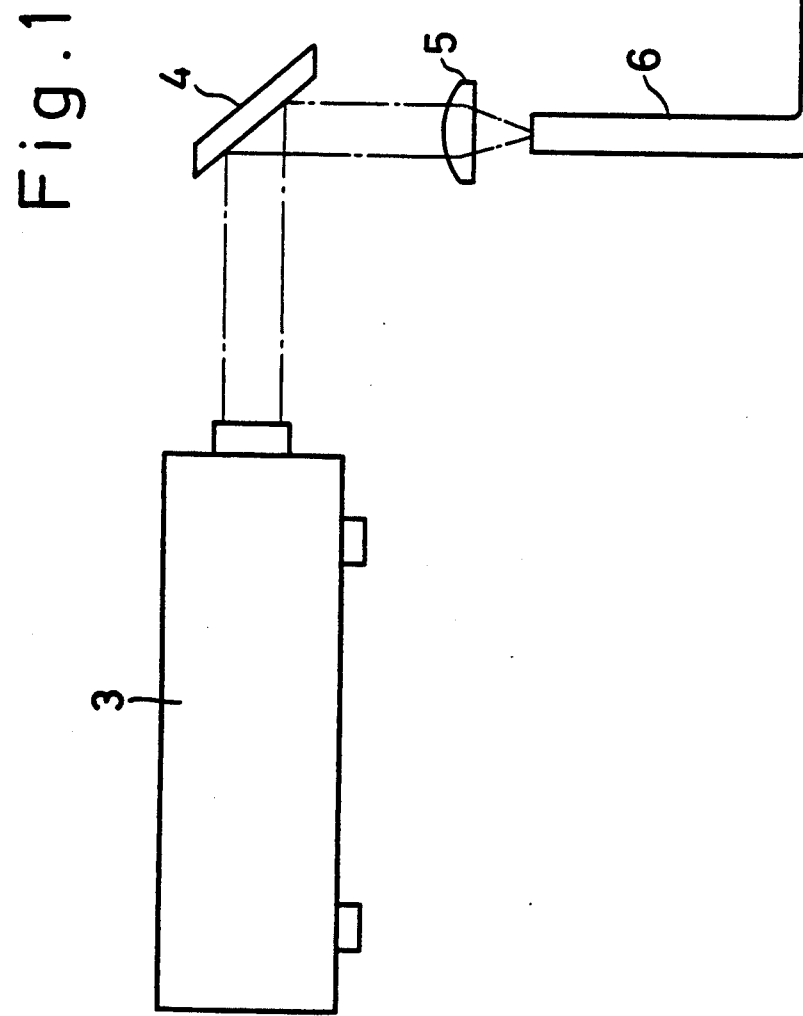

Then, the proximal end portion of the needle material 100, that is, its peripheral wall surrounding the mounting hole 100a, is annealed by means of an apparatus shown in FIG. 1, thereby lowering the hardness of the proximal end portion. Incidentally, the needle material 100 has fiber-like crystals because of the above cold drawing, and in order to soften the needle material 100 by changing its crystals into a grain-like shape, it is necessary to heat the needle material 100 up to 850° C. to 1,200° C.

Referring to FIG. 1, a rotary disk 1 has an axis of rotation disposed horizontally, that is, disposed parallel to the sheet of FIG. 1. V-shaped grooves 1a are formed in the outer peripheral surface of the rotary disk 1, and are circumferentially spaced from one another at equal intervals. The needle materials 100 are received in the V-shaped grooves 1a, respectively. The proximal end portion of the needle material 100 is projected axially from the side face of the rotary disk 1 by a predetermined distance longer than the mounting hole 100a. In a stationary condition of the rotary disc 1, the needle material 100 is held in position by a vertically-movable holder member 2.

The apparatus of FIG. 1 comprises an oscillator (e.g. YAG laser oscillator) 3 for outputting a laser beam. A laser beam (CW laser beam) of a continuous wave emitted from the oscillator 3 is composed of parallel rays, and is reflected by a mirror 4, and is condensed by a condenser lens 5, and is fed into one end of a fiber 6. The fiber 6 is called "a graded index-type fiber", and comprises a core and a clad layer enclosing the core. The above condensed laser beam is incident on one end face of the core of the fiber 6. The laser beam passes through the core of the fiber 6, and goes out of the other end of the core in a spreading manner, and is again condensed by condenser lenses 7 to be directed toward a focus F.

The focus F of the condenser lenses 7 is spaced a predetermined distance D from the proximal end face of the needle material 100 held by the rotary disk 1 and the holder member 2. Therefore, the laser beam converged on the focus F is directed toward the proximal end face of the needle material 100 in a spreading manner, and is converted into thermal energy there By continuing the supply of this laser beam, for example, for about 1 second, the proximal end portion of the needle material 100 is annealed.

In this embodiment, there is used the laser beam of the continuous wave type which is lower in peak value than a pulsed laser beam. And besides, as is well known, the fiber 6 of the graded index type has the function of lowering the peak value of the laser beam to smooth the laser beam. Therefore, an instantaneously-high thermal energy will not be applied to the proximal end portion of the needle material 100, and a uniform thermal energy is supplied to the needle material 100. This achieves a good annealing.

The distance D between the proximal end face of the needle material 100 and the focus F of the laser beam is much longer than the distance between the proximal end face and the focus of the first-mentioned laser beam used to create the mounting hole 100a, and the area of irradiation of the former laser beam at the proximal end face of the needle material 100 is greater. Therefore, the distribution of the thermal energy applied by the laser beam to the proximal end face of the needle material 100 is relatively gentle, and an excessive concentration of the thermal energy on the center of the proximal end face does not occur. Namely, because of the characteristics of the laser beam, although the energy is high at the central portion, and decreases progressively toward the peripheral portion, the distribution of this energy becomes gentler with increase of the area of irradiation of the laser beam. As a result, a good annealing can be effected.

In this embodiment, since the optical axis X of the laser beam lying between the other end of the fiber 6 and the proximal end face of the needle material 100 is in alignment with the axis of the needle material 100, a spot of the laser beam on the proximal end face of the needle material 100 is concentric with the proximal end face of the needle material 100. Therefore, the supplied thermal energy can be distributed uniformly over the proximal end portion of the needle material 100 in the direction of the periphery of the proximal end portion.

As shown in FIG. 1, by causing the area of irradiation of the laser beam at the proximal end face of the needle material 100 to substantially coincide with the area of the proximal end face of the needle material 100, the radial distribution of supply of the thermal energy at the proximal end face of the needle material 100 can be made gentle as much as possible, and also the laser beam can be used efficiently.

Figure 2:
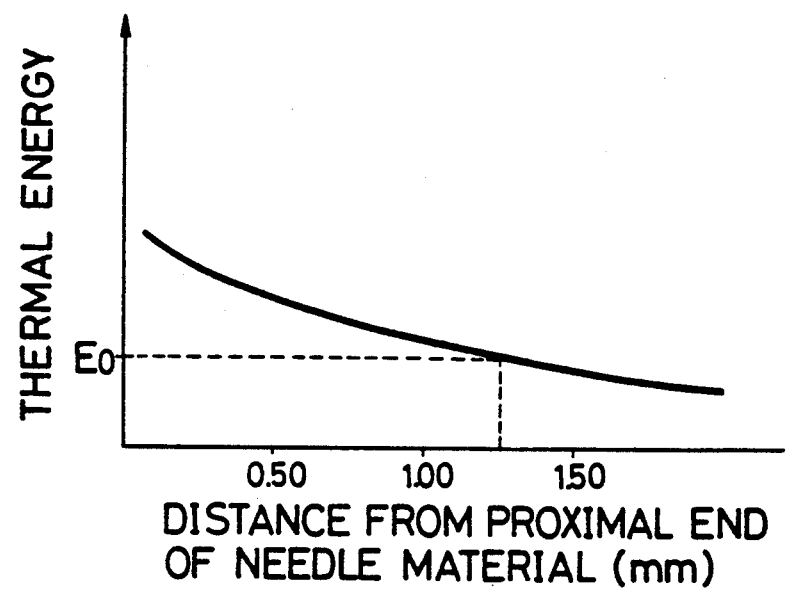
FIG. 2 is a graph showing a distribution of thermal energy applied to a needle material when annealing it.
Figure 3:
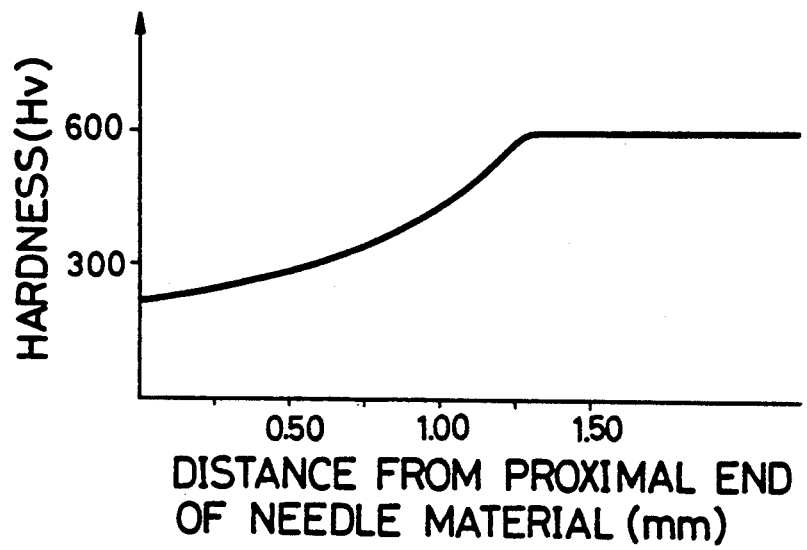
FIG. 3 is a graph showing a distribution of the hardness of the needle material after the annealing.

FIG. 2 shows the distribution of the supplied thermal energy in the direction of the length of the needle material when the annealing is effected. Here, the overall length of the needle material 100 is 20 to 25 mm, and the depth of the mounting hole 100a is about 1.25 mm. Since the laser beam is supplied to the proximal end face of the needle material 100, it will be readily appreciated that the supplied thermal energy is the highest at the proximal end of the needle material 100, and decreases progressively away from the proximal end of the needle material 100. The thermal energy received by that portion of the needle material 100 corresponding to the bottom end (i.e., closed end) of the mounting hole 100a is substantially equal to a minimum thermal energy Eo required for achieving the annealing temperature. The above supplied thermal energy causes a hardness distribution shown in FIG. 3. As is clear from this hardness distribution, the hardness of the needle material 100 is the lowest at its proximal end, and becomes higher progressively from the proximal end toward the distal end of the needle material 100. That portion of the needle material 100 corresponding to the bottom end of the mounting hole 100a is substantially equal in hardness to that portion of the needle material 100 not annealed (i.e., the portion except for the proximal end portion).

Various conditions required for obtaining the above hardness distribution will now h=described specifically with respect to a needle material (first example) having an inner diameter of 0.05 mm and an outer diameter of 0.55 mm and a needle material (second example) having an inner diameter of 0.05 mm and an outer diameter of 0.30 mm. Input voltages of the oscillator 3 are 240 V and 230 V, respectively, with respect to the first and second examples, and output energies are 10 W and 8 W, respectively, with respect to the first and second examples. In each of the two examples, the distance D between the focus F and the proximal end of the needle material 100 is 1.0 mm. The time periods of irradiation of the laser beam are 1.0 second and 0.9 second, respectively, with respect to the first and second examples.

Figure 4:
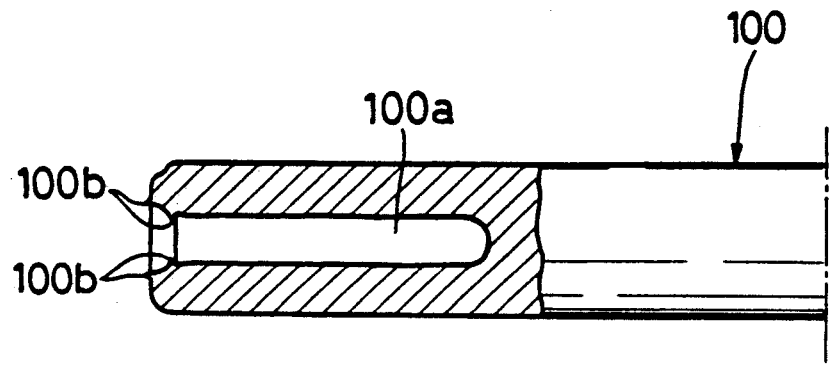
FIG. 4 is an enlarged, partly cross-sectional, side-elevational view of a proximal end portion of the needle material after the formation of a mounting hole.
Figure 5:
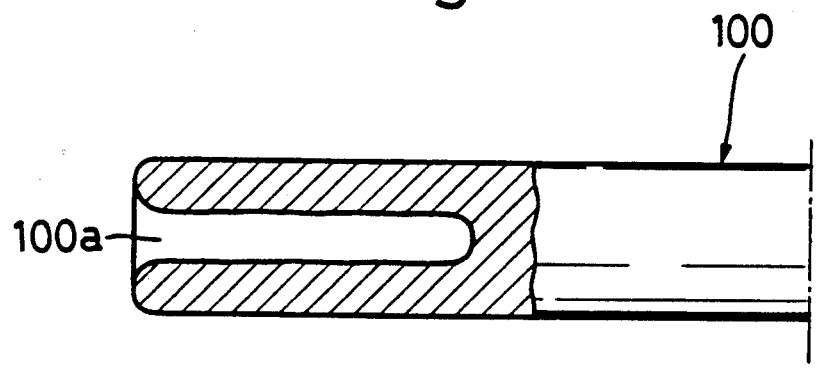
FIG. 5 is a view similar to FIG. 4, but showing a condition after the annealing.
Figure 6:
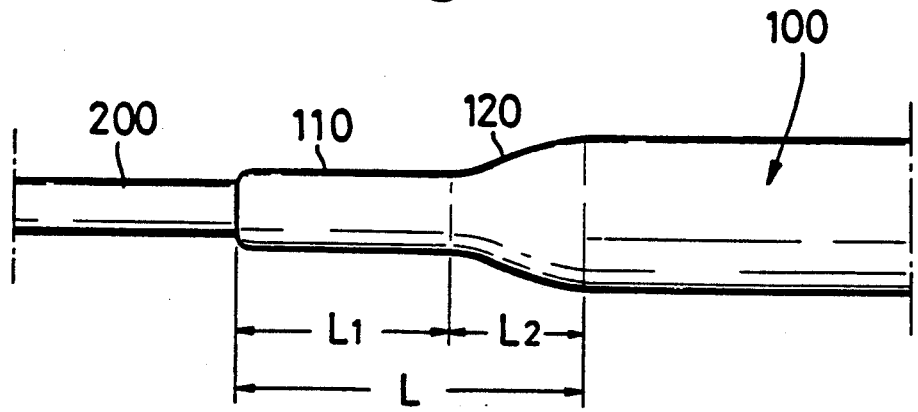
FIG. 6 is an enlarged, side-elevational view of the proximal end portion of the needle material after a gut is secured thereto.

Variation or change of the proximal end portion of the needle material 100 will now be described with reference to FIGS. 4 to 6 which show the sequence of the operation. FIG. 4 shows a condition in which the mounting hole 100a has been formed in the proximal end portion of the needle material 100, but the annealing is not yet applied to the proximal end portion. As shown in FIG. 4, sharp burrs and projections 100b are present on the inner and outer peripheral edges of the proximal end of the needle material 100. Such burrs and projections 100b are fused and removed by the thermal energy supplied when effecting the annealing, so that the inner and outer peripheral surfaces of the proximal end are smoothly curved, as shown in FIG. 5. After the annealing, one end portion of a gut 200 is inserted into the mounting hole 100a, and in this condition the proximal end portion of the needle material 100 is radially inwardly deformed or pressed by a pair of dies, as shown in FIG. 6. A semi-cylindrical groove and a tapered groove continuous therefrom are formed in each of the opposed surfaces of the pair of dies. Therefore, after this deformation, the proximal end portion of the needle material 100 has a cylindrical portion 110 of a reduced diameter having a length L1 extending from the proximal end, and a tapered portion 120 of a length L2 extending from the cylindrical portion 110. The overall length L (=L1+L2) of this deformed portion is substantially equal to the depth of the mounting hole 100a.

Effects of the annealing will now be discussed. After the formation of the mounting hole 100a, the laser beam is applied to the proximal end face of the needle material 100 to effect the annealing, and therefore the burrs and projections 100b, produced on the proximal end of the needle material 100 when forming the mounting hole 100a, are fused and removed. This advantageously eliminates the possibility that the gut 200 to be secured to the proximal end portion is cut by the burrs and projections 100b on the proximal end of the needle material 100. Also, since there exits no burr or projection projecting radially from the outer peripheral surface of the needle material 100, the ability of the suture needle to penetrate will not be affected. Further, there is not required any special working or processing for removing the above burrs and projections.

As described above, the hardness distribution shown in FIG. 3 can be obtained by applying the laser beam to the proximal end face of the needle material 100 to effect the annealing. That portion (extending over the length L1 in FIG. 6) of the proximal end portion required to be deformed in a larger amount has a sufficiently low hardness, and therefore the deformation can be effected satisfactorily to provide the cylindrical portion 110. And besides, there is eliminated the possibility that any portion of a high hardness remains at the proximal end, thereby ensuring a good deformation of the proximal end portion.

Although that portion extending over the length L2 (FIG. 6) increases in hardness progressively away from the proximal end, this portion can be satisfactorily deformed into the tapered portion 120, because the amount of deformation of this portion decreases progressively away from the proximal end. In other words, that region of the proximal end portion shorter than the depth of the mounting hole 100a is low in hardness, with the hardness of the tapered portion 120 increasing progressively away from the proximal end, and therefore the proximal end portion of the needle material 100 can have an increased mechanical strength.

When effecting the annealing, since the laser beam is applied only to the proximal end face of the needle material 100, pits and projections and an oxide film which would adversely affect the penetrating ability of the needle will not be formed on the outer peripheral surface of the proximal end portion of the needle material 100. Therefore, electropolishing can be omitted, or the time for such electropolishing can be shortened.

In the embodiment of FIG. 1, in the case where the oscillator 3 emits the laser beam of a continuous wave as described above, the use of the fiber 6 may be omitted, and the proximal end of the need material may substantially coincide with the focus of the condenser lenses 7. In the case where the oscillator 3 emits a pulsed laser beam, at least one of the two requirements, that is, the passage of the laser beam through the fiber 6 and the spacing of the proximal end of the needle material 100 from the focus of the condenser lenses 7, must be met.

Figure 7:
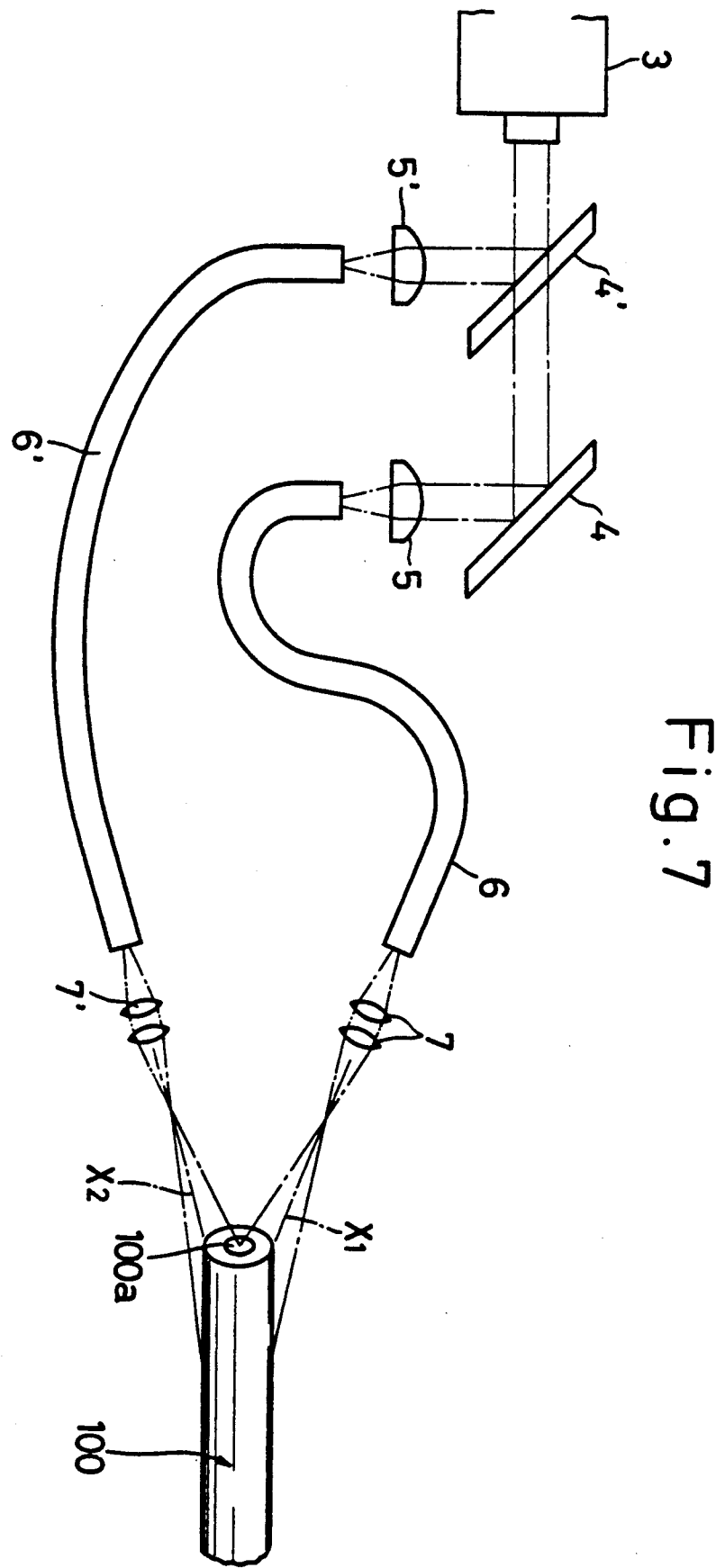
FIGS. 7 and 8 are schematic views showing modified apparatuses, respectively.

FIG. 7 shows another embodiment of the invention. Those portions of this embodiment corresponding respectively to those in FIG. 1 are denoted respectively by identical reference numerals, and explanation of such corresponding portions is omitted. In this embodiment, a semi-transparent mirror 4' is disposed between an oscillator 3 and a mirror 4, and a half of the energy of a laser beam is reflected by the semi-transparent mirror 4', and is supplied to one end of another fiber 6' of the graded index type via another condenser lens 5'. This separated laser beam passes through the fiber 6' and is condensed by condenser lenses 7'. A pair of laser beams, emitted respectively from the pair of fibers 6 and 6' and condensed respectively by the condenser lenses 7 and 7', have respective optical axes X1 and X2 inclined relative to the axis of the needle material 100. The inclination angles of the axes X1 and X2 are equal to each other, and are in the range of between 20° to 60°. The axes X1 and X2 are spaced 180° from each other circumferentially of the needle material 100.

In the embodiment of FIG. 7, each of the laser beams is applied to part of the proximal end face of the needle material 100 and part of the outer peripheral surface of the proximal end portion of the needle material 100. Therefore, the distribution of the supplied thermal energy can be gentler in the direction of the length of the needle material 100 than that of FIG. 1, and hence the hardness distribution can be gentler, and the region of a low hardness can be made longer. This embodiment is useful particularly when forming a deep mounting hole 100a in the needle material 100. In this embodiment, since the laser beams are also applied to the outer peripheral surface of the proximal end portion of the needle material 100, small pits and projections and an oxide film are formed thereon; however, this outer peripheral surface can be made smooth by a short-time electropolishing.

In FIG. 7, for the sake of simplicity of the description, although the pair of laser beams are applied to the needle material, more than two laser beams can, of course, be applied to the needle material. For example, in the case where three laser beams are used, the optical axes of the three laser beams are spaced 120° form one another circumferentially of the needle material.

Figure 8:
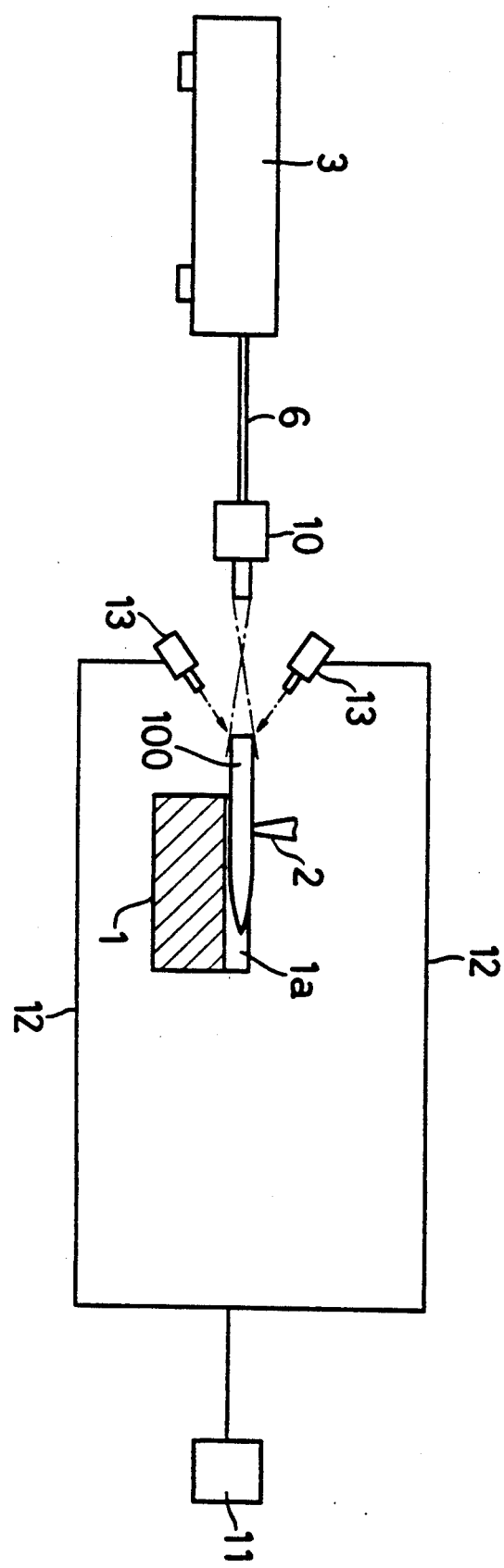

FIG. 8 shows a further embodiment of the invention. This embodiment is basically similar in construction to the embodiment of FIG. 1. A condenser lens corresponding to the condenser lens 5 of FIG. 1 is accommodated within a housing of an oscillator 3. Condenser lenses corresponding to the condenser lenses 7 of FIG. 1 are accommodated within a casing 10. The casing 10 is connected to the oscillator 3 via a fiber 6. In this embodiment, there is provided a bomb 11 filled with inert gas such as nitrogen gas and argon gas. A pair of nozzles 13 are connected to the bomb 11 via tubes 12. The nozzles 13 inject the inert gas to the proximal end face of the needle material 10 and those portions adjacent thereto, so that the annealing is effected in an atmosphere of the inert gas. By doing so, the formation of an oxide film on the proximal end face of the needle material 100 is prevented. The annealing in the atmosphere of the inert gas can, of course, be applied to the embodiment of FIG. 7.

FIGS. 9 and 10 shows a still further embodiment of the invention. In this embodiment, the formation of the mounting hole and the annealing are carried out by the same apparatus. More specifically, a rotary disk 1 supporting the needle materials 100 is supported on a frame 30 through a rotatable shaft 1b, and the frame 30 is mounted on a movable table 31. The movable table 31 is supported on a base 32 by a suitable means, such as a ball thread mechanism (not shown), so as to be movable relative to the base 32 along the axis of the needle material 100. A mechanism for vertically moving a holder member 2 is also mounted on the movable table 31.

An optical axis Xo of a laser beam of parallel rays emitted from an oscillator 3 is in alignment with the axis of the needle material 100. Disposed between the oscillator 3 and the needle material 100 are a light path converter 33 and condenser lenses 34 for condensing the laser beam of parallel rays. The light path converter 33 includes a pair of mirrors 3a and 33b, and each of the mirrors 33a and 33b is pivotal about one end thereof.

The apparatus shown in FIGS. 9 and 10 includes a fiber 35 of the graded index type disposed in spaced apart relation to the optical axis Xo. One end of the fiber 35 is disposed in registry with one mirror 33a whereas the other end of the fiber 35 is disposed in registry with the other mirror 33b. A condenser lens 36 is disposed between the one end of the fiber 35 and the mirror 33a, and a collimator lens 37 is disposed between the other end of the fiber 35 and the mirror 33b.

In the above construction, first, for forming the mounting hole 100a, the movable table 31 is located in a first position shown in FIG. 9. More specifically, the proximal end of the needle material 100 is disposed either at the focal position of the condenser lenses 34 or slightly spaced therefrom. The mirrors 33a and 33b of the light path converter 3 are disposed parallel to the optical axis Xo of the laser beam. In this condition, when the oscillator 3 emits one pulse of laser beam, this laser beam passes past those regions adjacent to the mirrors 33a and 33b, and directly reaches the condenser lenses 34 by which the laser beam is condensed and is supplied to the center of the proximal end face of the needle material 100, thereby forming the mounting hole 100a.

Then, the annealing is effected. More specifically, as shown in FIG. 10, the movable table 31 is moved away from the oscillator 3 into a second position. In this second position, the proximal end face of the needle material 100 is spaced a distance D from the focus F of the condenser lenses 34. Also, in the light path converter 33, the mirrors 33a and 33b are pivotally moved through 45° in clockwise and counterclockwise directions, respectively. In this condition, the oscillator 3 outputs 1,000 pulses of laser beam per second. This pulsed laser beam is reflected by the mirror 33a, and passes through the condenser lens 36, the fiber 35 and the collimator lens 37, and is reflected by the mirror 33b, and is further converged by the condenser lenses 34 toward the focus F, and then is fed from the focus F to the proximal end face of the needle material 100 in a spreading manner, thereby effecting the annealing. The smoothing effect achieved by the fiber 35 and the effect achieved by the spacing of the proximal end face of the needle material 100 from the focus F have already been described above, and therefore explanation of such effects is omitted here.

In this embodiment, for effecting the annealing, instead of a laser beam of a continuous wave, a number of pulses of laser beam are outputted. When effecting the annealing, it is necessary to satisfy at least one of two requirements, that is, the conversion of the laser beam path and the movement of the needle material 100 along its axis. In the case where it is necessary to effect only the light path conversion, the manufacturing time can be reduced greatly.

In this embodiment, the formation of the mounting hole and the annealing are carried out using the oscillator for emitting the pulsed laser beam. At present, as far as the inventor of the present invention knows, there does not exist any oscillator which can be switched between one mode for emitting a laser beam of a continuous wave and another mode for emitting one or more pulses of laser beam; however, if such an oscillator is used, the formation of the mounting hole can be done by the pulsed laser beam, and the annealing can be done by the laser beam of a continuous wave, without the need for the conversion of the laser beam path and the movement of the needle material.

The present invention is not restricted to the above embodiments, and various modifications can be made. For example, as the energy beam for the annealing, a light beam from a halogen lamp, an electron beam, an ion beam, or a plasma jet can be used. Also, for the formation of the mounting hole, any of the above energy beams except for the above light beam, a water jet, or a drill can be used. In the case where the drill is used to form the mounting hole, the annealing is carried out prior to the formation of the mounting hole.

What is claimed is:

1. A method of manufacturing an eyeless suture needle, comprising the steps of:
   (a) forming a mounting hole in a proximal end face of a needle material in such a manner that said mounting hole extends along an axis of said needle material, a gut being adapted to be inserted into and fixed to said mounting hole; and
   (b) applying an energy beam to the proximal end face of said needle material to anneal a proximal end portion of said needle material.

2. A method according to claim 1, in which the axis of said energy beam applied to said needle material is in alignment with the axis of said needle material.

3. A method according to claim 2, in which an area of irradiation of said energy beam at the proximal end face of said needle material is substantially equal to the area of said proximal end face.

4. A method according to claim 1, in which said step (b) comprising applying a plurality of energy beams to said needle material in such a manner that the axis of each of said plurality of energy beams is inclined relative to the axis of said needle material, the axes of said plurality of energy beams being spaced from one another in a direction of the periphery of said needle material, and said plurality of energy beams being applied not only to the proximal end face of said needle material but also to an outer peripheral surface of the proximal end portion of said needle material.

5. A method according to claim 4, in which the axes of said plurality of energy beams are inclined at the same angle relative to the axis of said needle material, and are spaced at equal intervals from one another in the direction of the periphery of said needle material.

6. A method according to claim 5, in which the angle of inclination of the axis of each of said energy beams relative to the axis of said needle material is in the range of between 20° to 60°.

7. A method according to claim 1, in which said annealing is carried out in an atmosphere of inert gas.

8. A method according to claim 1, in which the formation of said mounting hole is carried out by concentrating another energy beam on the center of the proximal end face of said needle material, the axis of said another energy beam being in alignment with the axis of said needle material, and said annealing being carried out after the formation of said mounting hole.

9. Apparatus for manufacturing an eyeless suture needle comprising:
(a) emitting means for emitting a pulsed laser beam of parallel rays;
(b) support means for supporting a needle material in such a manner that the axis of said needle material is in alignment with the optical axis of said laser beam;
(c) condenser means for condensing said laser beam, said condenser means being disposed in the vicinity of a proximal end face of said needle material, supported by said support means, in such a manner that an axis of said condenser means is in alignment with the optical axis of said laser beam;
(d) smoothing means for smoothing said pulsed laser beam, said smoothing means being spaced from the optical axis of said laser beam;
(e) switching means disposed between said emitting means and said condenser means so as to switch a path of travel of said laser beam between a first light path and a second light path, said switching means first selecting said first light path and then selecting said second light path; when said laser beam from said emitting means travels along said first light path, said laser beam passing past said switching means to reach said condenser means, so that said laser beam condensed by said condenser means is applied to the center of the proximal end face of said needle material to thereby form a mounting hole in said proximal end face, a gut being adapted to be inserted into and fixed to said mounting hole; and when said laser beam from said emitting means travels along said second light path, said laser beam passing through said smoothing means to be smoothed and further passing through said condenser means to be applied to the proximal end face of said needle material to thereby anneal said needle material.

10. Apparatus according to claim 9, in which said switching means comprises a pair of first and second mirrors each pivotal between an operative position and an inoperative position, said first mirror being disposed close to said emitting means whereas said second mirror is disposed remote from said emitting means; when said first light path is selected, each of said first and second mirrors being disposed in said inoperative position where said mirror is displaced from the optical axis of said laser beam from said emitting means; and when said second light path is selected, each of said first and second mirrors being disposed in said operative position where said mirror is disposed on the optical axis of said laser beam from said emitting means, so that said first mirror reflects said laser beam from said emitting means to direct said laser beam to said smoothing means whereas said second mirror reflects said laser beam passing through said smoothing means to direct said laser beam to said condenser means.

11. Apparatus according to claim 10, in which said smoothing means comprises a fiber of the graded index type having a core, a condenser lens being disposed between one end of said fiber and said first mirror so as to direct said laser beam, reflected by said first mirror, to said core of said fiber, and a collimator lens being disposed between the other end of said fiber and said second mirror so as to bring said laser beam, going out of said core, into a beam of parallel rays.

12. Apparatus according to claim 11, further comprising moving means for moving said support means along the axis of said needle material between a first position and a second position, said support means being first disposed in said first position when said mounting hole is to be formed, and then being disposed in said second position when said annealing is to be effected, and the proximal end face of said needle material being remoter from the focus of said condenser means in said second position than in said first position.

13. Apparatus for manufacturing an eyeless suture needle comprising:
(a) emitting means for emitting a pulsed laser beam of parallel rays;
(b) support means for supporting a needle material in such a manner that the axis of said needle material is in alignment with the optical axis of said laser beam;
(c) condenser means for condensing said laser beam, said condenser means being disposed in the vicinity of a proximal end face of said needle material, supported by said support means, in such a manner that an axis of said condenser means is in alignment with the optical axis of said laser beam; and
(d) moving means for moving said support means along the axis of said needle material between a first position and a second position, said support means being first disposed in said first position, and then being disposed in said second position; in said first position, said laser beam from said emitting means being condensed by said condenser means to be applied to the center of the proximal end face of said needle material to thereby form a mounting hole in said proximal end face, a gut being adapted to be inserted into and fixed to said mounting hole, and the proximal end face of said needle material being remoter from the focus of said condenser means in said second position than in said first position, so that said laser beams from said condenser means is spreaded over the proximal end face of said needle material to thereby anneal a proximal end portion of said needle material.

* * * * *